(12) United States Patent
MacDonald et al.

(10) Patent No.: US 7,914,536 B2
(45) Date of Patent: Mar. 29, 2011

(54) BONE REPAIR DEVICE AND METHOD

(75) Inventors: Joel MacDonald, Salt Lake City, UT (US); Jonathan Rose, North Salt Lake, UT (US)

(73) Assignees: Aesculap AG, Tuttlingen (DE); University of Utah Research Foundation, Salt Lake City, UT (US)

( * ) Notice: Subject to any disclaimer, the term of this patent is extended or adjusted under 35 U.S.C. 154(b) by 1126 days.

(21) Appl. No.: 11/077,910

(22) Filed: Mar. 11, 2005

(65) Prior Publication Data

US 2006/0217735 A1 Sep. 28, 2006

(51) Int. Cl.
*A61B 17/88* (2006.01)
(52) U.S. Cl. ............... 606/86 A; 606/104; 606/279
(58) Field of Classification Search .......... 606/246, 606/60, 250–279, 86 R, 86 A, 86 B, 99, 104, 606/105, 916; 81/451; 403/1, 6–9, 341, 403/377
See application file for complete search history.

(56) References Cited

U.S. PATENT DOCUMENTS

| | | | |
|---|---|---|---|
| 4,130,152 A * | 12/1978 | Bolen | 81/451 |
| 5,219,349 A * | 6/1993 | Krag et al. | 606/53 |
| 5,484,440 A * | 1/1996 | Allard | 606/916 |
| 5,536,268 A * | 7/1996 | Griss | 606/254 |
| 5,672,176 A | 9/1997 | Biedermann et al. | |
| 5,782,833 A | 7/1998 | Haider | |
| 5,810,816 A | 9/1998 | Roussouly et al. | |
| 6,740,086 B2 | 5/2004 | Richelsoph | |
| 6,858,030 B2 * | 2/2005 | Martin et al. | 606/86 A |
| 2002/0091386 A1 * | 7/2002 | Martin et al. | 606/61 |
| 2002/0095153 A1 * | 7/2002 | Jones et al. | 606/61 |
| 2004/0138662 A1 * | 7/2004 | Landry et al. | 606/61 |
| 2004/0143265 A1 * | 7/2004 | Landry et al. | 606/61 |
| 2004/0236330 A1 | 11/2004 | Purcell et al. | |
| 2004/0243126 A1 * | 12/2004 | Carbone et al. | 606/61 |
| 2004/0267264 A1 | 12/2004 | Konieczynski et al. | |

FOREIGN PATENT DOCUMENTS

| | | |
|---|---|---|
| DE | 41 27 303 C2 | 2/1993 |
| DE | 19726754 | 2/1999 |
| EP | 0528177 | 2/1993 |
| EP | 1090595 | 4/2001 |

OTHER PUBLICATIONS

Aesculap Spine S4 Spinal System Instrumentation Guide.
Aesculap Socon SRI Spondylolisthesis Reduction Instrument The Finer Points, Jeffrey Kozak, MD, 2002.
Int'l. Search Report for PCT/EP2006/002060 dated May 30, 2006.

* cited by examiner

*Primary Examiner* — Eduardo C Robert
*Assistant Examiner* — Tara R Carter
(74) *Attorney, Agent, or Firm* — RatnerPrestia

(57) ABSTRACT

A device for repairing a bone disorder using a polyaxial screw. The device has a pivoted lever mounted rotatably to an extension of a bone screw and which extends essentially at right angles to the longitudinal direction of the extension to which it is mounted and is in contact with a stop on the other extension associated with the vertebral body to be repositioned. The extension that acts on the polyaxial bone screw comprises a longitudinal sleeve, a rod, preferably threaded, extending from within the sleeve and moveable within the sleeve, and a contact surface disposed on the end of the threaded rod which is configured to transmit a force against the bone screw to prevent polyaxial movement of the polyaxial bone screw for as long as the force is transmitted.

11 Claims, 8 Drawing Sheets

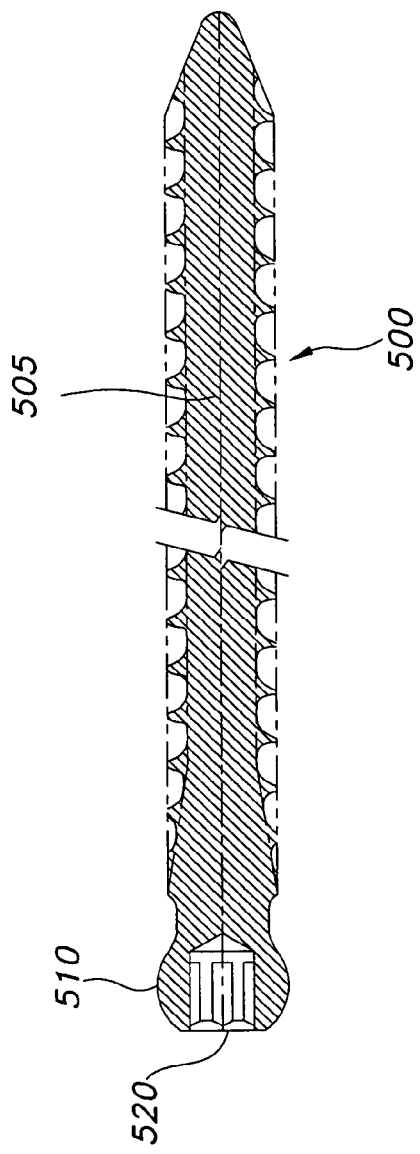
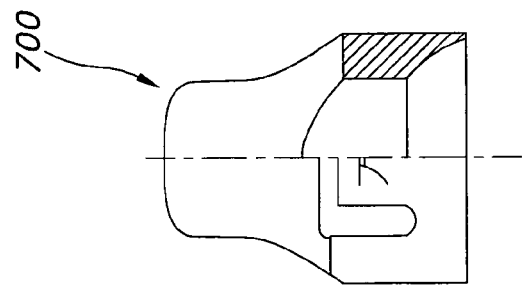
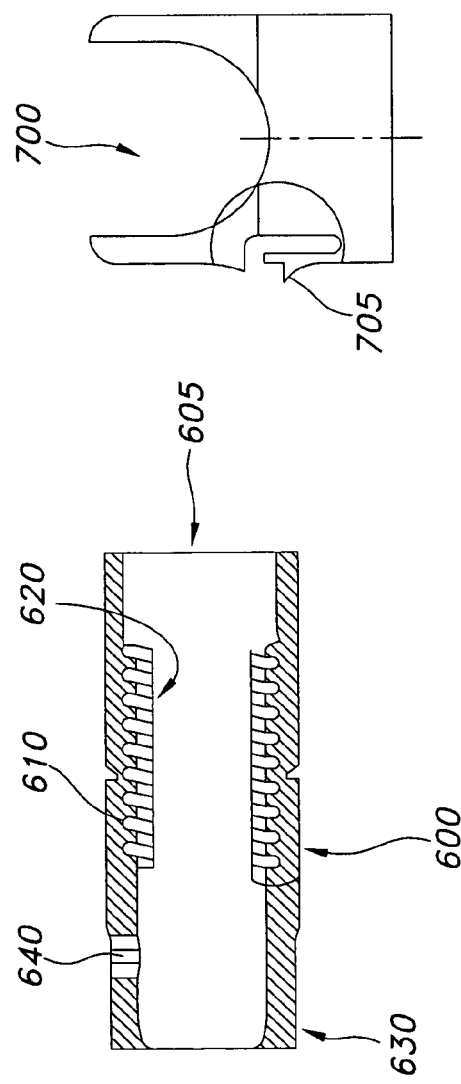
FIG. 5
FIG. 7A
FIG. 7B
FIG. 6

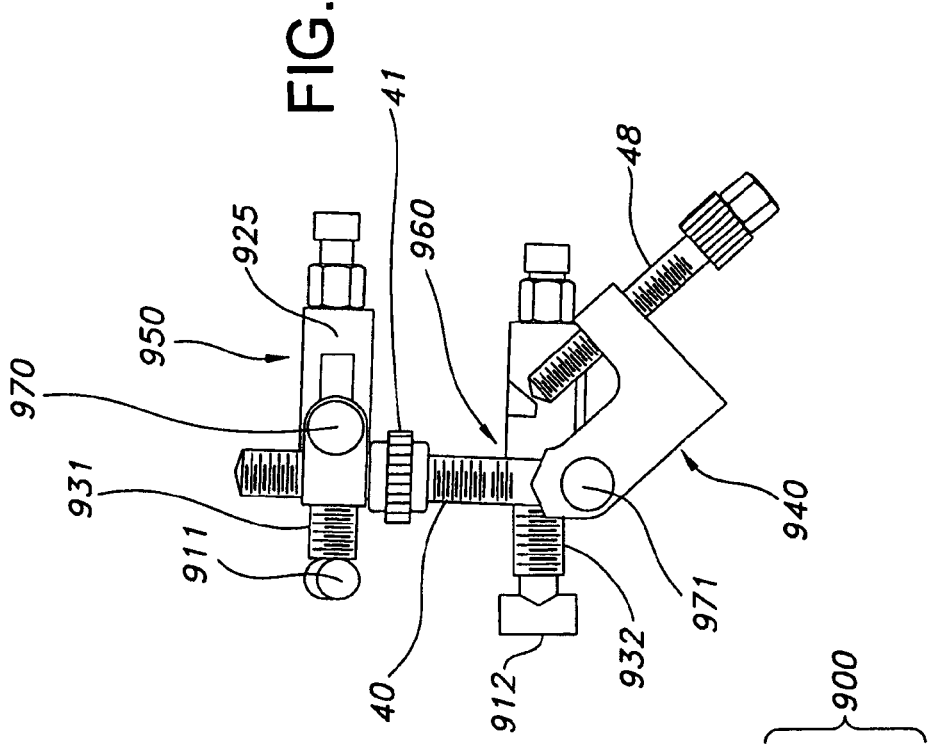
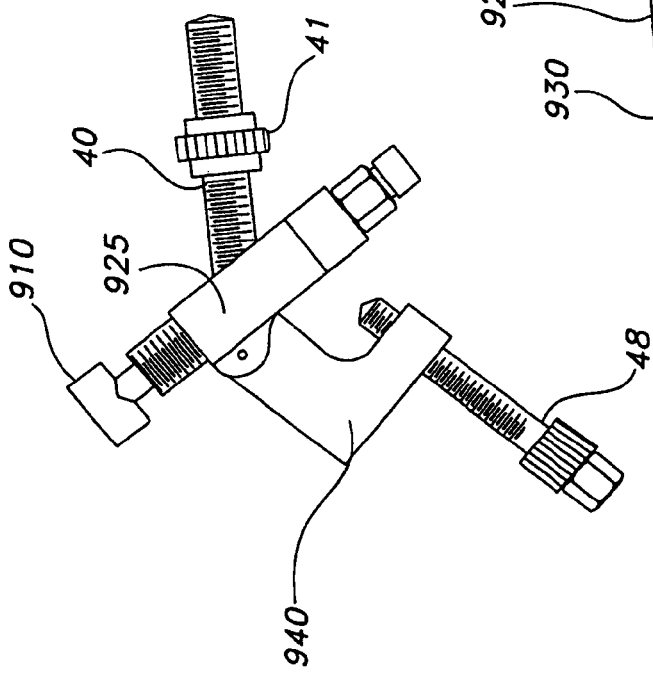

BONE REPAIR DEVICE AND METHOD

FIELD OF INVENTION

The present invention relates to bone fixation devices, and more particularly to apparati and methods for spine repair.

BACKGROUND

The spinal column is a highly complex system of bones and connective tissues that provides support for the body and protects the delicate spinal cord and nerves. The spinal column includes a series of vertebrae stacked one atop the other, each vertebral body including an inner or central portion of relatively weak cancellous bone and an outer portion of relatively strong cortical bone. Situated between each vertebral body is an intervertebral disc that cushions and dampens compressive forces experienced by the spinal column. A vertebral canal containing the spinal cord and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease or trauma, such as ruptured or slipped discs, degenerative disc disease, fractured vertebra, and the like. Patients that suffer from such conditions usually experience extreme and debilitating pain, as well as diminished nerve function.

An exemplary spinal treatment for some of the above problems involves immobilizing the spine by using orthopedic rods, commonly referred to as spine rods, that run generally parallel to the spine. This may be accomplished by exposing the spine posteriorly and fastening bone screws to the pedicles of the appropriate vertebrae. The pedicle screws are generally placed two per vertebra and serve as anchor points for the spine rods. Clamping elements adapted for receiving a spine rod therethrough are then used to join the spine rods to the screws. The aligning influence of the rods forces the spine to conform to a more desirable shape. In certain instances, the spine rods may be bent to achieve the desired curvature of the spinal column.

SUMMARY

The present invention provides a device for repairing a bone disorder, and in particular for repositioning a vertebrae, such as in a spondylolisthesis reduction. The device includes a screw extension having a longitudinal sleeve, a moveable rod extending from within the sleeve and moveable within the sleeve, and a contact surface disposed on the end of the rod which is configured to transmit a force against the head of the polyaxial bone screw to prevent movement of the polyaxial bone screw for as long as the force is transmitted. Preferably, the contact surface is a contact rod disposed perpendicular to the longitudinal axis of the threaded rod, and the contact rod is free to rotate around a central axis which is the same as the longitudinal axis of the threaded rod. An alternative embodiment has the contact surface being a torque applying means which contacts the screw head directly.

Also included is a fixation device for the repair of a bone disorder, the fixation device having at least one polyaxial bone screw that can be screwed into the vertebral body to be repositioned, and at least one other bone screw that can be screwed into an adjacent bone, which bone screws are connected with one another in an articulated manner by means of a cross strut, the bone screws having extensions which extend in their longitudinal direction, the extensions having free ends and opposite ends that act on the bone screws with a tightening device that applies a tensile force on one of the two bone screws, wherein the tightening device has a pivoted lever mounted rotatably to an extension of one of the bone screws and which extends essentially at right angles to the longitudinal direction of the extension to which it is mounted and is in contact with a stop on the other extension associated with the vertebral body to be repositioned, characterized in that the extension that acts on the at least one polyaxial bone screw comprises a longitudinal sleeve, a threaded rod having an end, the threaded rod extending from within the sleeve and rotatable within the sleeve, and a contact surface disposed on the end of the threaded rod which is configured to transmit a force against the bone screw to prevent polyaxial movement of the polyaxial bone screw for as long as the force is transmitted.

Also included is a method for repairing a bone disorder, such as a spondylolisthesis, comprising inserting a polyaxial screw into a vertebral bone, the polyaxial screw comprised of a screw and a cap, applying a force on the head of the polyaxial screw to prevent polyaxial rotation of the screw within the cap, adjusting the vertebra having the screw with respect to an adjacent vertebrae, removing the force on the head of the polyaxial screw to allow polyaxial rotation of the cap with respect to the screw, and securing a rod to the polyaxial screw cap to thereby fix the repositioned vertebrae.

BRIEF DESCRIPTION OF THE FIGURES

The features of the invention believed to be novel and the elements characteristic of the invention are set forth with particularity in the appended claims. The figures are for illustration purposes only and are not necessarily drawn to scale. The invention itself, however, both as to organization and method of operation, may best be understood by reference to the detailed description which follows taken in conjunction with the accompanying drawing in which:

FIG. 5 shows a screw in accordance with the present invention;

FIG. 6 shows a polyaxial screw cap in accordance with the present invention;

FIGS. 7A and 7B show a bone screw polyaxial insert in accordance with the present invention;

FIG. 8 shows a fixation device with a screw extension mounted in accordance with the present invention;

FIG. 9 shows the screw extension of the present invention;

FIG. 10 shows a fixation device with two screw extensions mounted in accordance with the present invention;

DETAILED DESCRIPTION OF INVENTION

Figure 1:
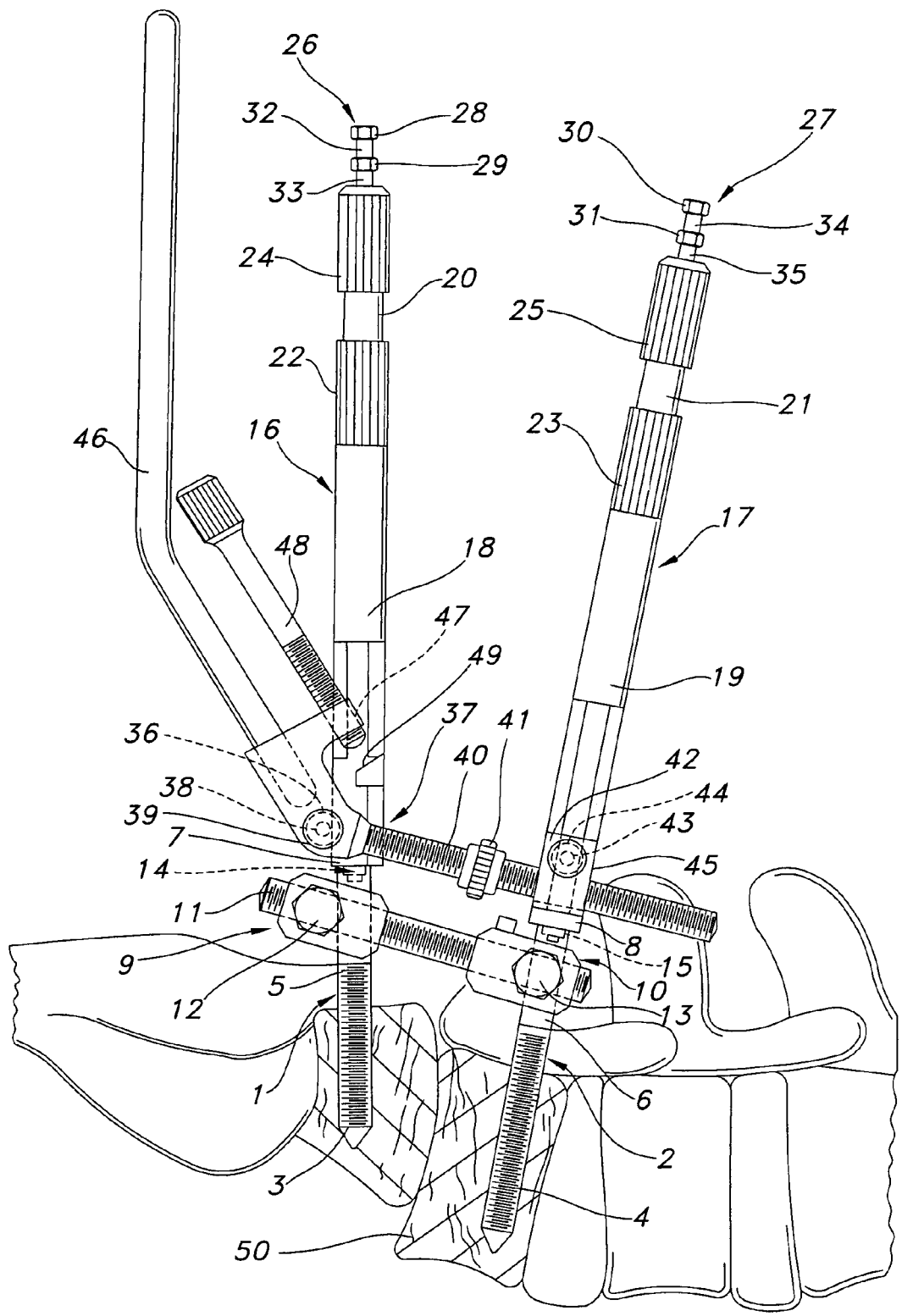
FIG. 1 shows a fixation device screwed in the spine with a repositioning instrument prior to the repositioning of the vertebral body, in accordance with the prior art.

The present invention generally involves a technique commonly referred to as spinal fixation whereby surgical implants are used for fusing together and/or mechanically immobilizing vertebrae of the spine. Spinal fixation may also be used to alter the alignment of adjacent vertebrae relative to one another so as to change the overall alignment of the spine.

The invention is directed in large part to isthmic and degenerative spondylolisthesis, which is a common cause of lumbar symptomatology and one of the most common indications for lumbar reconstruction. One of the keys to safe reduction is the careful, controlled application of force and limited distraction amounting to no more than physiological disc space height. A successful instrument and method for reduction in accordance with this variable was developed by Aesculap and is known commercially as the SOCON® spondylolisthesis reduction instrument. (SOCON is a registered trademark of Aesculap AG for a fixation device for repositioning a lumbar spondylolisthesis with bone screws and rods.)

More particularly, such a device includes a bone screw that can be screwed into a vertebral body to be repositioned, and a bone screw that can be screwed into an adjacent bone (adjacent vertebral body), which screws are connected by a cross strut via portions of each screw that protrude from the bones in an articulated manner, wherein the articulated connections between the bone screws and the cross strut can be fixed. The device includes extensions that act on the bone screws and extend in the longitudinal direction of the bone screws, which extensions are connected to a tightening, adjustment device, which applies a tensile force on at least one of the two bone screws.

This object of that development was accomplished by the tightening device which had a pivoted lever mounted rotatably at the extension of one of the bone screws, which pivoted lever extended essentially at right angles to the longitudinal direction of the extension and was in contact with a stop of the other extension associated with the vertebral body to be repositioned. This aspect of the device will be understood more fully in accordance with the drawings and description below.

Essentially, the tensile force was transmitted by the pivoted lever. That lever was mounted at the extension, which was associated with the bone part that was not to be repositioned. In other words, the tensile forces were introduced from the mounting site of the pivoted lever directly into the bone part that is not to be repositioned, which thus forms an abutment for the entire device. That was typically the vertebral body that was adjacent to the vertebral body for which repositioning was necessary. In particular, with the development of that device, it became unnecessary that the cross strut act as an abutment for the tightening device, so that the pivoted connections between the cross strut and the extensions remained separate during the repositioning of the vertebral body.

Figure 2:
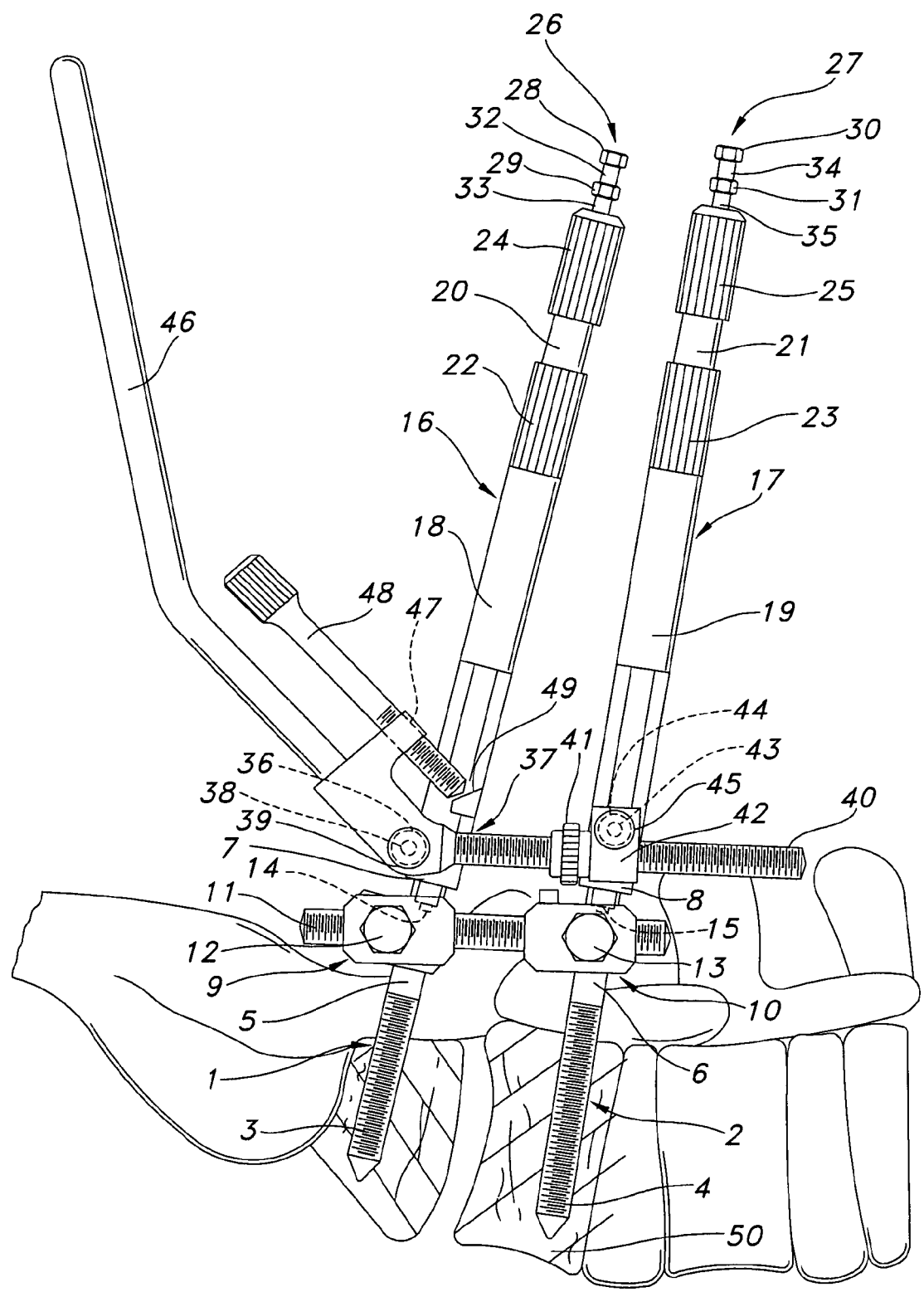
FIG. 2 shows a view similar to that in FIG. 1 after the repositioning of the vertebral body.
Figure 3:
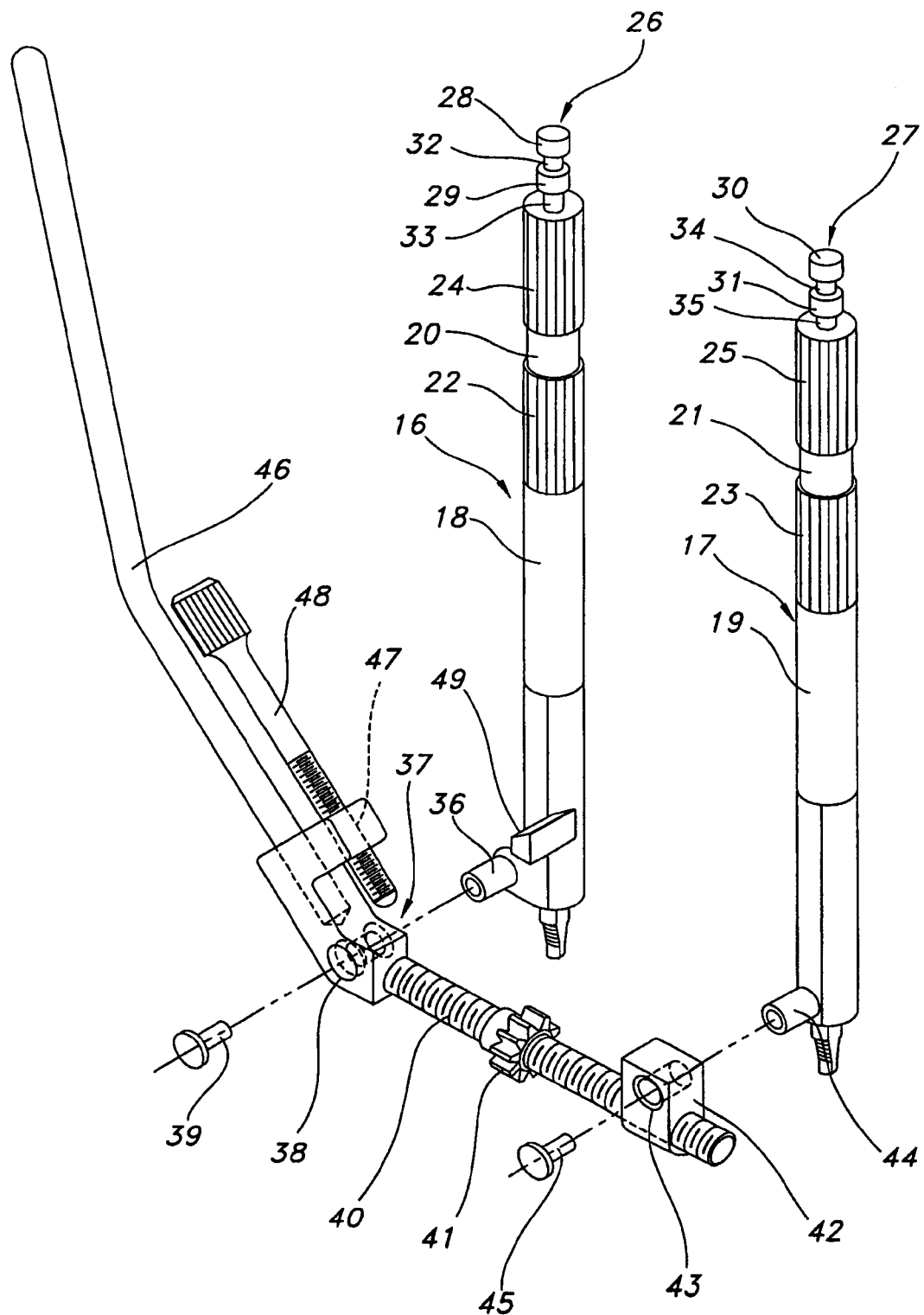
FIG. 3 shows a perspective view of the parts forming the repositioning device before the assembly.

Specifically, and turning now to FIGS. 1-3, which are prior art, it can be seen that this device comprised two bone screws 1, 2 with a respective screw-in thread 3 and 4 and with a smooth shank portion 5 and 6, respectively, which adjoined the screw-in thread and which were limited by a collar 7, 8 projecting in a flange-like manner.

A clamping piece 9 and 10, respectively, was pushed over shank 5, 6 of each bone screw 1, 2, respectively. The two clamping pieces 9 and 10 were passed through by a cross strut 11, which was a threaded rod that extended essentially at right angles to the longitudinal direction of the bone screws 1 and 2.

The cross strut 11 was screwed into the clamping pieces 9, 10 and fixed in the axial direction as a result. Both clamping pieces 9 and 10 had clamping screws 12 and 13, which made possible the pivoting of the cross strut 11 in relation to the bone screws 1, 2 in the detached state, doing so about an axis that extended at right angles to the plane extending through the cross strut and the bone screws. By tightening the clamping screws 12 and 13, the clamping pieces 9 and 10 could be fixed such that the pivoting of the cross strut 11 in relation to the bone screws 1 and 2 was prevented.

Both bone screws 1, 2 had an internal threaded hole 14 and 15, respectively, into which a respective extension 16 and 17 was screwed, at their ends, facing away from the respective screw-in thread 3 and 4. Both extensions had an elongated sleeve 18 and 19, respectively, through which extended a fixing screw 20, 21, which were screwed into the respective internal threaded holes 14 and 15 of the respective bone screws 1 and 2. The sleeves 18, 19 carried in their upper end areas respective flutings 22 and 23, and respective flutings 24 and 25 were likewise arranged at the upper ends of the fixing screws 20, 21 in the areas projecting from the respective sleeves 18 and 19.

At the free ends of the fixing screws 20 and 21 were pin-shaped extensions 26 and 27, respectively, with two parallel collars 28, 29 and 30, 31, respectively. The grooves or offsets 32, 33 and 34, 35, respectively, which were formed between these collars, were used as a working surface for a prior-art distraction instrument, not shown in the drawings. Such a distraction instrument optionally carried, for example, hooks, which could be inserted into the grooves and which were held by the branches of the forceps-like instrument.

Insofar as the parts of the fixation device have been described so far, the corresponding parts were essentially all of symmetrical design, i.e., the clamping pieces inserted into the extensions and screwed onto the bone screws are of an identical design; these assembly units of an identical design are connected with one another by the cross strut.

Turning now to a non-symmetrical aspect of the prior-art device shown in FIGS. 1-3, upon which the present invention improves (which improvement will be discussed in more detail below), a vertically projecting bearing bolt 36, on which a two-armed lever 37 is mounted pivotably, is arranged at a lower end of sleeve 18. A screw 39 passing through a bearing bore 38 at the lever 37 is used for fixing on the bearing bolt 36. This can best be seen in FIG. 3.

An arm 40 of the lever 37 is designed as a threaded rod, on which a knurled nut 41 is screwed. The arm 40 dips, furthermore, into a bearing sleeve 42, in which the arm 40 is displaceable in the longitudinal direction. The bearing sleeve 42 has a bearing bore 43, and the latter is in turn mounted rotatably on a bearing bolt 44, which is arranged in parallel to the bearing bolt 36, but at the sleeve 19 of the other extension. The bearing sleeve 42 is fixed by a screw 45 screwed into the bearing bolt 44.

The other arm 46 of the lever 37 forms an angle of about 135° with the arm 40; it is bent, in turn, so that the free end of the arm 46 points approximately in the direction of the bone screws and the extensions. See especially FIG. 1.

An adjusting screw 48, which can be brought with its free end into contact with a fixed stop 49 of the sleeve 18, is screwed into an internal threaded section 47 of the lever 37, which threaded section extends essentially in parallel to the arm 46. When the adjusting screw 48 is in contact with the stop 49, a pivoting movement of the lever 37 is blocked in one direction, in the clockwise direction in the exemplary embodiment shown in FIGS. 1 and 2.

During use of the prior art instrument described, the two bone screws 1 and 2 are at first inserted, one bone screw being inserted into the vertebral body 50 to be repositioned, and the other bone screw being inserted into an adjacent bone, for example, an adjacent vertebral body or into the hip bone. The screwing in of the screws is performed laterally in relation to the central longitudinal plane of the spine.

After the bone screws 1 and 2 have been screwed in, the clamping pieces 9 and 10 with the cross strut 11 are attached to the shanks 5 and 6 of the bone screws 1 and 2, respectively. The clamping pieces 9 and 10 remain loosened, i.e., the cross strut is pivotable in relation to the bone screws 1 and 2, but the distance between the two clamping pieces 9 and 10 is fixed by the cross strut 11.

The sleeves 18 and 19, respectively, are subsequently attached to the bone screws 1 and 2, respectively, by means of the fixing screws 20 and 21 and fixed there. The two-armed lever 37 acts on both sleeves 18 and 19 in the manner described. This initial position of the operation is shown in FIG. 1. The adjusting screw 48 is now moved away from the stop 49, and the knurled nut 41 is located at a spaced location from the bearing sleeve 42.

The spine is extended by distraction in a first step of the method. The pin-shaped extensions 26 and 27 of the two sleeves 18 and 19, respectively, are acted on for this purpose, and the ends of these sleeves 18 and 19 are brought close to one another by means of a suitable distraction instrument. Due to the distance of the assembly units comprising the bone screw and the extension, which distance is fixed by the cross strut 11, the spine is expanded, on the one hand, and adjusted by a slight tilting of the vertebral body 50 to be repositioned, on the other hand. Because the clamping pieces 9 and 10 are not fixed, the two assembly units can be pivoted in relation to one another to an extent. The lever 37 does not hinder this distraction in any way, and the arm 40 slides during the distraction in the bearing sleeve 42, which can freely adjust its angular position in relation to the sleeve 19.

The desired repositioning of the vertebral body 50 takes place after the distraction by pivoting the two-armed lever 37 in such a way that the arm 40 exerts an upwardly directed tensile force on the sleeve 19 and consequently the bone screw 2. This can be achieved in a simple manner by pivoting the lever clockwise (FIGS. 1 and 2), wherein the bearing forces for the lever 37 are directly introduced into the bone acting as an abutment via the sleeve 18 and the bone screw 1.

As soon as the desired position of the vertebra has been reached, it can be fixed by bringing the adjusting screw 48 into contact with the stop 49 and by bringing the knurled nut 41 into contact with the bearing sleeve 42. The clamping screws 12 and 13 are subsequently tightened, so that the two bone screws 1 and 2 and the cross strut 11 will form a now rigid fixation for the vertebral body 50 to be repositioned. The extensions 16 and 17 can then be removed from the bone screws 1 and 2 by loosening the fixing screws 20 and 21, so that only the fixation device formed from the bone screws 1 and 2 and the cross strut 11 will remain in the body.

Provisions are made in a preferred embodiment of the device just described for the stop at the extension of the vertebral body to be repositioned to be pivoted about an axis that extends in parallel to the pivot axis of the lever. The stop preferably surrounds the lever here and is freely displaceable relative to the lever in its longitudinal direction. A pivotable bearing sleeve is thus obtained for the lever, which guides the lever at the extension of the vertebral body to be repositioned, on the one hand, and, on the other hand, transmits the tensile forces to the extension without hindering the pivoting of the extension during the distraction of the vertebrae.

Provisions may be made for the lever to have an external threaded section, on which a stop nut is screwed, in the area between the two extensions. The effective length of the lever between the articulation site of the said lever and the stop of the extension is thus fixed, so that during the pivoting of the lever, the cross strut and the lever, together with the extensions, form a parallelogram arm-like guide, which makes possible an essentially tilt-free transverse displacement of the vertebral body to be repositioned.

Provisions are made in a preferred embodiment for the extensions to be detachably connected with the bone screws. Contrary to conventional extensions, which are snipped off at the end of the operation, the extensions can be simply removed. They can also be reattached later, so that the repositioning may possibly also be performed in steps. Sharp areas, which are formed due to the extensions being pinched off in conventional extensions and could possibly lead to injuries, are avoided as a result.

In particular, the extensions may have sleeves, at which the lever and the stop are mounted. These sleeves are held at the bone screws by fixing screws, which extend through the sleeves and can be screwed into the bone screws.

The extensions may additionally have offsets at their free ends for receiving a distraction instrument, by means of which distraction of the spine is performed prior to the repositioning proper in order to create the space that is needed for the repositioning in the first place for the vertebral body to be repositioned.

Figure 4:
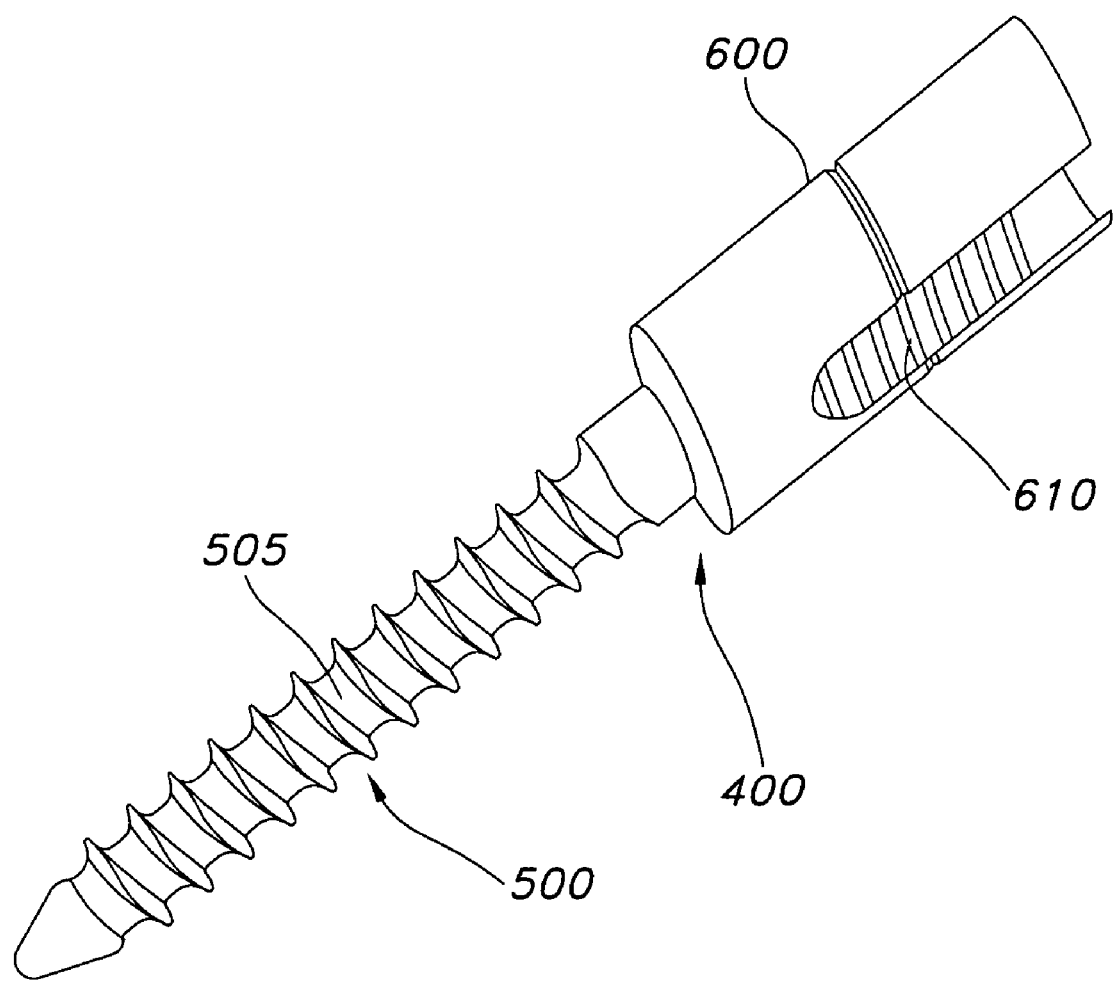
FIG. 4 a polyaxial screw system in accordance with the present invention.

The present invention improves upon the design just described by adding additional features. FIG. 4 shows a polyaxial bone screw system 400. FIG. 5 shows an exemplary bone screw 500; FIG. 6 shows threaded bone screw cap 600; and FIGS. 7A and 7B show bone screw polyaxial insert 700. Together these three pieces comprise polyaxial bone screw system 400.

In this exemplary embodiment, bone screw 500 has threaded shaft 505 and a semi-spherical head 510 with a recess 520 defined therein to receive torque-applying means such as a hex-head wrench or screwdriver. Bone screw 500 would be inserted into threaded bone screw cap 600 in the direction of arrow 605 shown in FIG. 6, which bone screw cap 600 has internal threads 610 along an internal surface portion 620. Internal threads 610 are configured to receive a set screw (not shown). Bone screw cap 600 has an inwardly tapered end portion 630 sized to prevent bone screw 500 from passing through bone screw cap 600 but still allow polyaxial rotation of bone screw 500 when held within bone screw cap 600.

After bone screw 500 is placed into bone screw cap 600, bone screw polyaxial insert 700 is inserted and affixed within bone screw cap 600. As shown in FIG. 7A, bone screw polyaxial insert 700 has protrusion 705 which mates with hole 640 in bone screw cap 600 to lock or affix bone screw polyaxial insert 700 into place within bone screw cap 600 and thereby anchor bone screw 500 within the system while still allowing bone screw 600 to rotate polyaxially. The completed assembly is shown in FIG. 4, although bone screw polyaxial insert 700 can not be seen because it is within the lower portion of bone screw cap 600. FIG. 4 also shows internal threads 610.

In order for this polyaxial screw system to operate, the screw is inserted into a bone, at which point the polyaxial bone screw cap 600 is allowed to freely rotate (or revolve) around the screw head. Once a rod is placed into the channel of the screw cap, it is compressed downward by virtue of the application of a set screw into the internal threads of the screw cap 600, which compresses the bone screw polyaxial insert 700 against the upper portion of the screw head, which locks the orientation of the screw cap against the screw and thereby anchors everything together solidly. Many such methods and devices for securing a rod in a screw cap are known to those skilled in the art.

Turning now to the invention with more particularity, it is noted that polyaxial screw systems (one type of which is noted above) and the fixation device noted above with respect to FIGS. 1-3 have been combined, with modifications to be discussed, to form the present invention. FIG. 8 shows such a combination of a fixation device generally in accordance with that discussed above (but with modifications to be addressed below) and a polyaxial screw system.

Specifically, in this embodiment, the fixation device of the prior art as discussed above has been modified as a part of the present invention to allow for connection to a polyaxial screw assembly like that shown in the exemplary embodiment of FIG. 4. FIG. 9 shows an extension for the device for use with a polyaxial screw. Specifically, the extension includes an engaging arm 900 with compression bar 910 extending from rod 920 having threaded portion 930. Rod 920 in the embodiment shown is comprised of threaded portion 930 rotatable within rod sleeve 925. Compression bar 910 is essentially a portion of a rod which will later be seated within the polyaxial screw system upon fixation in accordance with the above. Compression bar 910 is a preferred contact surface of rod 920, although other configurations could be used depending on the geometry of the particular polyaxial screw system to be used.

In the case illustrated, compression bar 910 is disposed perpendicular to the longitudinal central axis of rod 920 but is rotatable around the central longitudinal axis of screw engaging arm 900. Thus, as the threaded portion 930 rotates into screw cap 600, compression bar 910 is moved longitudinally with respect to rod sleeve 925, but remains in a single rotational orientation. Threaded portion 930 can be rotated by applying a rotational force (or torque) on opposite end 934. Also shown as a part of polyaxial screw engaging arm 900 in FIG. 9 is arm sleeve 935 which receives arm 40 of adjustment (fixation) device 940.

Other means exist for progressively advancing and locking the compression bar 910 away from rod sleeve 925, such as a ratcheting system or other such means. The key is that the contact surface or area be able to be advanced and locked against the screw head, or polyaxial screw insert, and then be removable again by a reversal of that force. A preferred embodiment to achieve this is a threaded rod.

FIG. 10 shows an exemplary device having two polyaxial screw engaging arms 950 and 960 attached to arm 40 on either side of knurled nut 41 of adjustment device 940. Shown disposed on the ends of each polyaxial screw engaging arm 950 and 960, respectively, are compression bars 911 and 912. Also shown are threaded portions 931 and 932, respectively. As noted above, each polyaxial screw engaging arm 950 and 960 is free to rotate about a center of rotation delineated as axis 970 and 971, respectively, in FIG. 10.

In an alternative embodiment, the contact surface could apply a force directly to the screw, instead of through the polyaxial insert. It is preferable in the case as noted above that the polyaxial insert be mated with the compression bar so that the force applied by the compression bar is evenly applied to the screw head by virtue of the shape of the polyaxial insert. It is possible, however, for the contact surface to be other than the compression bar embodiment and still be within the scope of the invention.

Figure 10A:
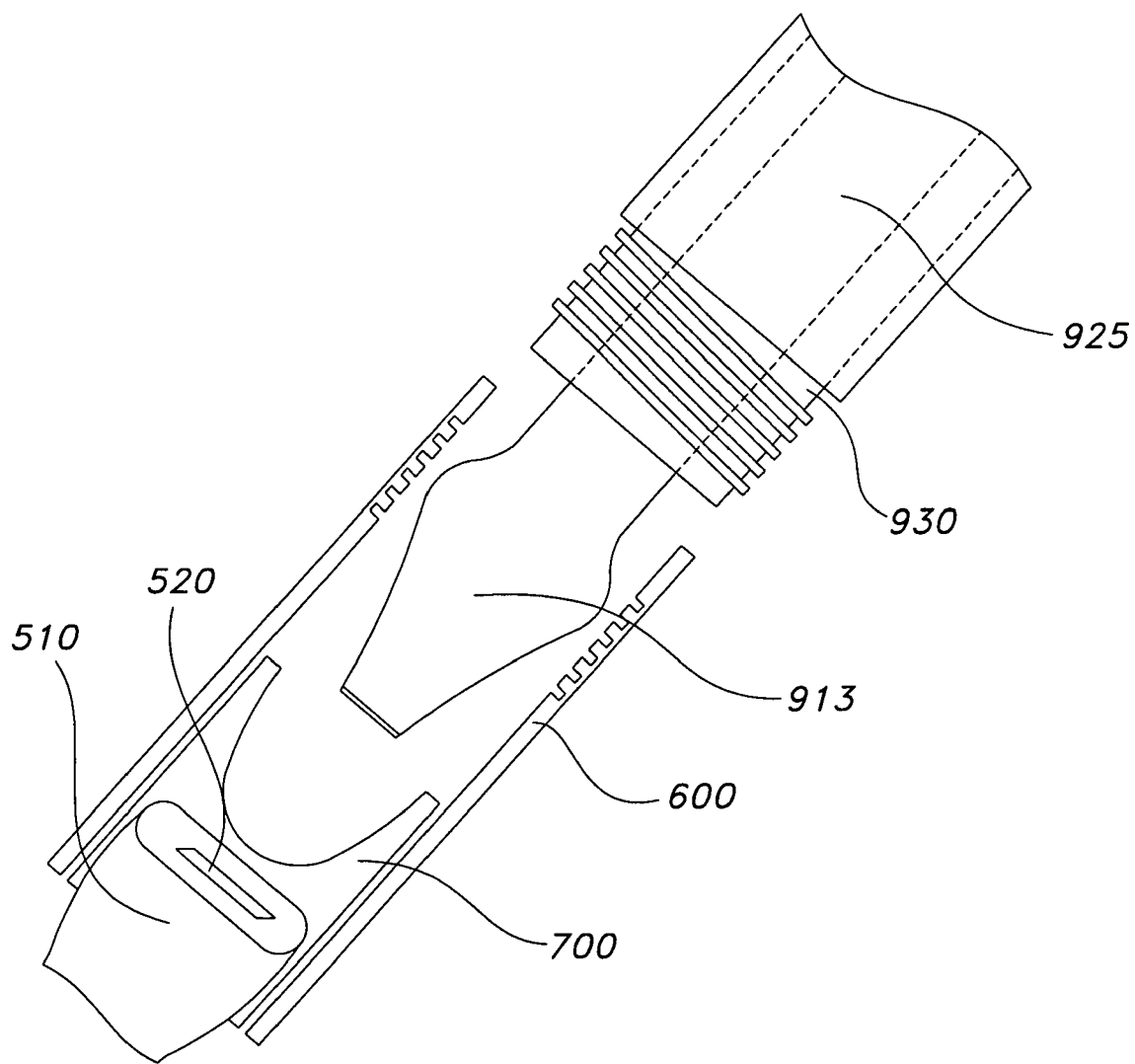
FIG. 10A shows an alternative embodiment of the present invention having a torque applying means as the rod contact surface.

In such an exemplary alternative embodiment, such as that shown in FIG. 10A, instead of compression bar 910 being advanced into a compressive relationship with polyaxial insert 700, a torque applying means could be used to contact screw head 510 directly, which torque applying means would then be locked by advancing threaded portion 930 into screw cap 600. FIG. 10A shows such an embodiment, where the screw contact surface disposed at the end of arm 900 is a torque applying means (a regular screwdriver head in this case) which matingly engages the screw head directly. In such a case, the polyaxial insert is not compressed during this locking step, but rather the screw head is contacted directly by the torque applying means 913, which is freely rotatable and longitudinally moveable within threaded portion 930 and sleeve 925. In this embodiment, when torque applying means is advanced as shown by the arrow in FIG. 10A, it contacts the screw head (not shown). Then, when threaded portion 930 is advanced downward into screw cap 600, it contacts and compresses torque applying means 913 which is subsequently prevented from moving within screw cap 600 or sleeve 925, thereby locking the system in place.

Figure 11:
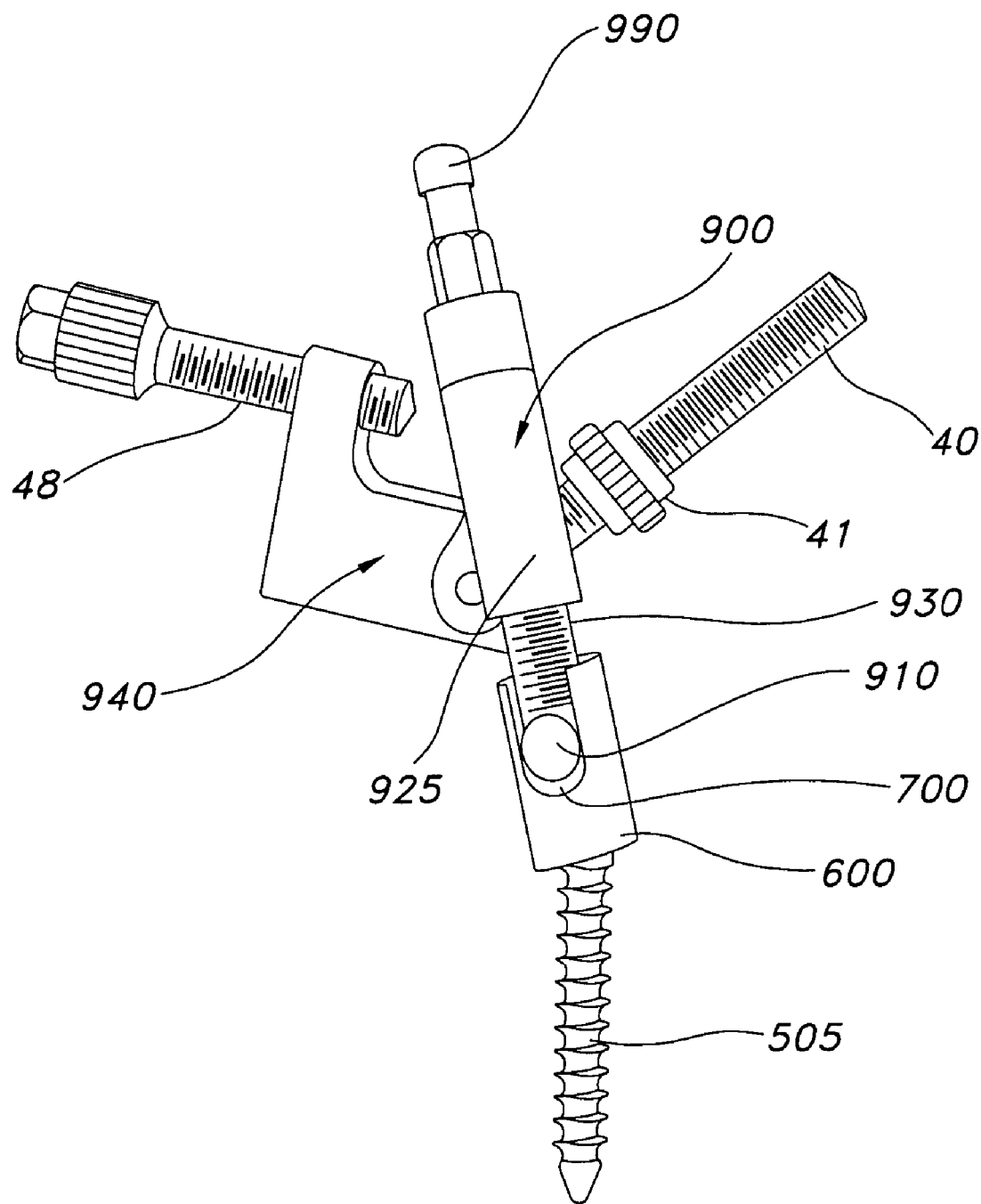
FIG. 11 shows the fixation device in accordance with the present invention having a polyaxial bone screw mounted thereto.

The device as described in accordance with the present invention allows the adjustment of a polyaxial screw system with an adjustment device heretofore only useable with non-polyaxial (mono-axial) screws. FIG. 11 shows the features of the present invention which allow the use of the adjustment device with polyaxial screws. Specifically, internal threads 620 of polyaxial bone screw cap 600 have received the threaded portion 930 of polyaxial screw engaging arm 900 a the threaded portion 930 was advanced out of rod sleeve 925. As can be seen from FIG. 11, as polyaxial bone screw cap 600 receives polyaxial screw engaging arm 900 as it is screwed in and advanced downward, the compression bar 910 exerts a force against bone screw polyaxial insert 700 in a downward direction, as can be seen in FIG. 11. Compression bar 910, in this embodiment, is screwed into place by rotating handle 990, although any appropriate means to apply a torque on threaded portion 930 would work.

The downward force applied to bone screw polyaxial insert 700 as the threaded portion 930 of polyaxial screw engaging arm 900 is threaded into internal threads 620 of polyaxial bone screw cap 600 causes the locking of the screw 500 with respect to bone screw cap 600 and a locked orientation thereof as described above. This process is performed for each of the polyaxial bone screws being used in a procedure. In some situations, it may be preferable to use only one polyaxial screw with another mono-axial screw, or multiple polyaxial screws with multiple mono-axial screws. The number and type of each screw would be determined based on the particular bone disorder being treated or repaired. In a typical spondylolisthesis reduction procedure in accordance with this invention, four (4) or six (6) such polyaxial screws would be used, although 2 or more could be used.

Once locked in accordance with the above, orientation of the bones in which the screws are inserted can proceed in accordance with the fixation device described above. After fixation orientation is achieved, polyaxial screw engaging arm 900 is unscrewed from bone screw cap 600, allowing once again free rotation of the cap with respect to the now-adjusted bone, at which point a rod can be placed into the bone screw cap and secured in accordance with known methods.

Also included is a method for repairing a bone disorder, such as a spondylolisthesis, comprising inserting a polyaxial screw into a vertebral bone, the polyaxial screw comprised of a screw and a cap, applying a force on the head of the polyaxial screw to prevent polyaxial rotation of the screw within the cap, adjusting the vertebra having the screw with respect to an adjacent vertebrae, removing the force on the head of the polyaxial screw to allow polyaxial rotation of the cap with respect to the screw, and securing a rod to the polyaxial screw cap to thereby fix the repositioned vertebrae.

It is also possible to secure a fixation rod within the polyaxial screw cap to fix the repositioned vertebrae before removing the force on the head of the polyaxial screw. This later embodiment would prevent any slight slippage of the vertebrae between the time the force is released and the fixation rod is placed.

In a preferred embodiment in accordance with the above, the present invention includes the method described wherein the step of applying a force includes screwing a contact rod down into the cap from an extension attached to a fixation device. In an alternative embodiment, and in accordance with that discussed above, the method may include applying a force by screwing a torque applying means down into the screw and compressing the torque applying means against the screw to thereby lock the screw and the cap in a fixed relationship.

The method is preferably performed by applying the force on the head of the polyaxial screw via a threaded rod being advanced within a sleeve into a screw cap to compress a contact surface against a screw cap insert, thereby locking the screw orientation with respect to the screw cap. Once the vertebral adjustment is made, the locking force against the head of the screw is removed by retracting the rod from the screw head insert in accordance with the above.

Although the present invention has been particularly described in conjunction with specific preferred embodiments, it is evident that many alternatives, modifications, and variations will be apparent to those skilled in the art. It is therefore contemplated that the appended claims will embrace any such alternatives, modifications, and variations as falling within the true scope and spirit of the present invention.

What is claimed is:

1. A method for repairing a spinal disorder comprising: inserting a polyaxial screw into a vertebral bone, the polyaxial screw comprised of a screw and a cap; applying a force on a head of the polyaxial screw by advancing a cylindrical contact rod down into the cap to prevent polyaxial rotation of the screw with respect to the cap, the contact rod having a longitudinal axis extending generally perpendicularly to the longitudinal axis of the cap; adjusting the vertebra having the screw with respect to an adjacent vertebrae; securing a rod to the polyaxial screw cap to thereby fix the repositioned vertebrae; and removing the force on the head of the polyaxial screw to allow polyaxial rotation of the cap with respect to the screw.

2. The method of claim 1 wherein the step of applying a force includes screwing the contact rod down into the cap from an extension attached to a fixation device.

3. The method of claim 1 wherein the step of applying a force includes screwing the contact rod down into the cap and compressing the contact rod against the screw to thereby lock the screw and the cap in a fixed relationship.

4. The method of claim 1 wherein the spinal disorder to be repaired is a spondylolisthesis.

5. An adjustment device for repositioning the orientation of bones prior to fixation, the adjustment device comprising at least one extension for attachment to a polyaxial screw assembly, the at least one extension comprising:
a generally cylindrical outer sleeve having a longitudinal axis;
a generally cylindrical inner sleeve extending through the outer sleeve coaxially with the longitudinal axis of the outer sleeve, the inner sleeve having a longitudinal bore extending therethrough and a threaded exterior section projecting from a distal end of the outer sleeve; and
a shaft extending through the bore of the inner sleeve, the shaft axially displaceable through the bore of the inner sleeve and rotatable relative to the inner sleeve, the shaft having a distal end with a compression contact surface, wherein the compression contact surface comprises a generally cylindrical bar for locking engagement with a polyaxial screw assembly, the bar having a longitudinal axis extending generally perpendicularly to the longitudinal axis of the outer sleeve.

6. The adjustment device of claim 5, wherein the inner sleeve is axially displaceable through the outer sleeve to axially advance the compression contact surface, the inner sleeve being displaceable between a distal position to force the compression contact surface into locking engagement with a polyaxial screw head, and a proximal position to disengage the compression contact surface from the polyaxial screw head.

7. The adjustment device of claim 5, wherein the at least one extension comprises:
a first extension, said outer sleeve being a first outer sleeve on the first extension, said inner sleeve being a first inner sleeve on the first extension, and said shaft being a first shaft on the first extension; and
a second extension interconnected to said first extension in an articulating arrangement, the second extension comprising:
a second outer sleeve having a longitudinal axis;
a second inner sleeve extending through the second outer sleeve, the second inner sleeve having a longitudinal bore extending therethrough and a threaded exterior section projecting from a distal end of the second outer sleeve; and
a second shaft extending through the bore of the second inner sleeve of the second extension, the second shaft axially displaceable through the bore of the second inner sleeve and rotatable relative to the second inner sleeve, the second shaft having a distal end with a compression contact surface.

8. The adjustment device of claim 7 comprising an arm interconnecting said first and second extensions in the articulating arrangement, said first extension comprising an arm sleeve that receives an end of the arm and allows axial displacement of the arm through the sleeve.

9. An adjustment device for repositioning the orientation of bones prior to fixation, the adjustment device comprising:
a generally cylindrical outer sleeve having a longitudinal axis;
a generally cylindrical inner sleeve extending through the outer sleeve along the longitudinal axis of the outer sleeve, the inner sleeve having a bore extending therethrough and a threaded outer section projecting from a distal end of the outer sleeve;
a shaft extending through the bore of the inner sleeve, the shaft axially displaceable through the bore of the inner sleeve and rotatable relative to the inner sleeve, the shaft having a distal end with a compression contact surface, the compression contact surface comprising a cylindrical bar for locking engagement with a polyaxial screw assembly, the bar having a longitudinal axis extending generally perpendicularly to the longitudinal axis of the outer sleeve; and
a screw cap for connection with a polyaxial bone screw, the screw cap having a bore into which the distal end of the shaft is inserted, the bore comprising internal threads engaged with the threaded outer section of the inner sleeve.

10. The adjustment device of claim 9, wherein the threaded outer section of the inner sleeve is rotatable in the bore of the screw cap to advance the compression contact surface into the inner sleeve and into engagement with a polyaxial screw head in the screw cap to lock the orientation of the polyaxial screw relative to the screw cap.

11. The adjustment device of claim 10, wherein the axial orientation of the shaft and bar are independent of the axial orientation of the inner sleeve such that the shaft and bar do not rotate as the inner sleeve is rotated.

* * * * *